(12) United States Patent
Fahrig et al.

(10) Patent No.: US 7,713,948 B2
(45) Date of Patent: May 11, 2010

(54) USE OF 5-SUBSTITUTED NUCLEOSIDES FOR REINFORCING THE APOPTOTIC EFFECT OF CYTOSTATIC DRUGS

(75) Inventors: Rudolf Fahrig, Hannover (DE); Joerg-Christian Heinrich, Dresden (DE); Georg Krupitza, Vienna (AT)

(73) Assignee: Resprotect GmbH, Dresden (DE)

( * ) Notice: Subject to any disclaimer, the term of this patent is extended or adjusted under 35 U.S.C. 154(b) by 536 days.

(21) Appl. No.: 10/550,013

(22) PCT Filed: Nov. 20, 2003

(86) PCT No.: PCT/EP03/13008

§ 371 (c)(1), (2), (4) Date: Apr. 4, 2006

(87) PCT Pub. No.: WO2004/084917

PCT Pub. Date: Oct. 7, 2004

(65) Prior Publication Data

US 2006/0178338 A1 Aug. 10, 2006

(30) Foreign Application Priority Data

Mar. 24, 2003 (DE) .................. 103 13 035

(51) Int. Cl.
*A61K 31/7072* (2006.01)
*A61K 31/70* (2006.01)
(52) U.S. Cl. .................. 514/50; 514/49; 514/51; 536/28.54
(58) Field of Classification Search .................. 514/50, 514/49, 51; 536/28.54
See application file for complete search history.

(56) References Cited

U.S. PATENT DOCUMENTS

| 6,589,941 B1 | 7/2003 | Fahrig et al. |
| 2004/0127454 A1 | 7/2004 | Fahrig et al. |

FOREIGN PATENT DOCUMENTS

| EP | 0806956 | 8/2002 |
| WO | 96/23506 | 8/1996 |
| WO | WO 96/23506 | * 8/1996 |
| WO | 01/07088 | 2/2001 |
| WO | 02/067951 | 9/2002 |

OTHER PUBLICATIONS

E. de Clercq, "Potential of Bromovinyldeoxyuridine in Anticancer Chemotherapy," Anticancer Research, vol. 6, No. 4, Jul. 1986, pp. 549-556.
R. Fahrig et al., "Prevention of adriamycin-induced mdr1 gene amplification and expression in mouse leukemia cells by simultaneous treatment with the anti-recombinogen bromovinyldeoxyuridine," Anti-Cancer Drug Design (2000),15(5), pp. 307-312 (incorrectly dated 2001 in the International Search Report).
M. Iigo et al., "Effect of (E)-5-(2-bromovinyl)-2'-deoxyuridine on Life-Span and 5-Fluorouracil metabolism in Mice with Hepatic Metastases," Euro. J. Cancer, vol. 26, No. 10, 1990, pp. 1089-1092.
B. Degreve at al., "Selection of HSV-1 TK Gene-Transfected murine Mammary Carcinoma Cells Resistant to (E)-5-(2-bromovinyl)-2'-deoxyuridine (BVDU) and ganciclovir (GCV)" Gene Therapy (2000), 7(18), pp. 1543-1552.
J. Balzarini, "Increased Sensitivity of Thymine Kinase Deficient (TK-) Tumor Cell Lines to the Cell Growth Inhibitory Effects of (E)-5-(2-bromovinyl)-2'-deoxyuridine (BVDU) and Related Compounds," Anticancer Research, vol. 6, No. 5, 1986, pp. 1077-1084.
S. Pancheva, "Methotrexate Potentiates Anti-Herpes Simplex Virus Type 1 Activity of E-5-(2-bromovinyl)-2'-deoxyuridine," Acta virologica, vol. 39, No. 2, 1995, pp. 117-119.
J. Kerr et al., "Apoptosis: A Basic Biological Phenomenon with Wide-Ranging Implications in Tissue Kinetics," Br. J. Cancer, (1972) 26, pp. 239-257.
R. Fahrig et al., "Induction or suppression of SV40 amplification by genotoxic carcinogens, non-genotoxic carcinogens, or tumor promoters," Mutation Research 356 (1996) 217-224.
R. Fahrig, "Anti-recombinogenic and convertible co-mutagenic effects of (*E*)-5-(2-bromovinyl)-2'-deoxyuridine (BVDU) and other 5-substituted neucleoside analogs in *S. cerevisiae* MP1," Mutation Research 372 (1996) 133-39.
Hodnick et al., "Measurement of Dicumarol-Sensitive NADPH:(Menadione-Cytochrome c) Oxidoreductase Activity Results in an Artifactual Assay of DT-Diaphorase in Cell Sonicates," Anal. Biochem. 252(1), 1997, 165-168.
Fahrig et al., *RP101 improves the efficacy of chemotherapy in pancreas carcinoma cell lines and pancreatic cancer patients*, Anti-Cancer Drugs 2006, 17:1045-1056.
Fahrig, et al., *Inhibition of Induced Chemoresistance by Cotreatment with (E)-5-(2-Bromovinyl)-2'-Deoxyuridine (RP101)*, Cancer Research 63, 5745-5753, Sep. 15, 2003.
U.S. Appl. No. 11/853,540, filed Sep. 11, 2007.

* cited by examiner

*Primary Examiner*—Shaojia Anna Jiang
*Assistant Examiner*—Michael C Henry
(74) *Attorney, Agent, or Firm*—Greenblum & Bernstein, P.L.C.

(57) ABSTRACT

The invention relates to the use of at least one overexpression inhibitor of DNA repair genes and oncogenes for producing a drug to increase the apoptotic effect of cytostatics after chemotherapy.

14 Claims, 6 Drawing Sheets

USE OF 5-SUBSTITUTED NUCLEOSIDES FOR REINFORCING THE APOPTOTIC EFFECT OF CYTOSTATIC DRUGS

BACKGROUND OF THE INVENTION

The invention relates to the use of at least one overexpression inhibitor of DNA repair genes and/or oncogenes for producing a drug to increase the apoptotic effect of cytostatics after chemotherapy.

Cancer diseases in humans are one of the most frequent causes of death and chemotherapy is the most frequent treatment method. The inadequate chances for a cure by a chemotherapy are based on the occurrence of resistances. These resistances have their root in the fact that cytostatics influence the expression of genes and have a genotoxic effect, i.e. induce mutations, gene amplifications and recombinations and hence destabilise the genome. In this way, a chemotherapy induces or selects resistant cancer cells. Often oncogenes, such as e.g. Ras, Bcl2, Bcr-abl, Myc, ErbB2 and others, are affected by such effects induced by cytostatics. Wrongly regulated expression of genes in conjunction with DNA repair and recombination also contributes to chemoresistance (e.g. p53 gene, BRCA1/2, UBE2N, APEX and Rad51), furthermore enzymes which metabolise and bioactivate cytostatics (e.g. DHFR, DT-diaphorase (DT-D), or proteins which convey cytostatics (e.g. MDR1).

Most cytostatics eliminate tumour cells in that they induce apoptosis. Apoptosis is a form of programmed cell death which was described firstly in Kerr, J. F. et al., Br J Cancer, 26(4) (1972); 239-257. In contrast to necrosis, apoptosis is a physiological form of cell death. These two forms of cell death can be differentiated by means of differences between necrosis and apoptosis. Apoptosis has defined morphological and biochemical characteristics which occur successively as events of an ordered cascade. The continuous process can be divided into phases. Morphological characteristics of apoptosis are core chromatin condensation (karyopyknosis), shrinkage of cytoplasm, formation of apoptotic vesicles and finally apoptotic bodies. Tumour cells can prevent this by overactivation of survival mechanisms. Mechanisms of chemoresistance therefore also comprise anti-apoptotic acting genes, such as e.g. STAT3, the activated "signal transducer and activator of transcription 3" or JUN-D.

In 1995 effects of specific hormones and 5-substituted nucleosides which were hitherto unknown were discovered. These suppress the 2-amino-6-mercaptopurine (AMP)-induced SV40 amplification in cells of the Chinese hamster (Fahrig, R. et al., Mutat Res., 356 (2), 1996, 217-224) and triethylene melamine-induced recombination in yeasts (Fahrig, R., Mutat Res, 372 (1), 1996, 133-139). In EP 0 806 956 B1, the treatment of leukaemia cells of the mouse with 5-substituted nucleosides is described, the doxorubicin (adriamycin)-induced Mdr1 gene amplification and chemoresistance having been inhibited.

In the in vitro tests implemented to date, 5-substituted nucleosides (i.e. base analogues) have always been applied together with one or more cytostatics.

DESCRIPTION OF THE INVENTION

Starting from the state of the art described here, it was the object of the present invention to prevent the reduction in apoptotic effect caused by resistance formation or at least to delay it and hereby to provide an improved treatment method relative to the forms of therapy known from the state of the art.

This object is achieved by the use described in claim 1. The further dependent claims demonstrate advantageous developments.

According to the invention, the use of at least one overexpression inhibitor of DNA repair gene and/or oncogene for producing a drug to increase the apoptotic effect of cytostatics after chemotherapy is provided.

Of concern here are above all the DNA repair genes UBE2N and/or APEX, DDX1, STAT3 and/or JUN-D are of concern as oncogenes.

Preferably, a 5-substituted nucleoside, the protected forms, salts or prodrugs thereof, is used as overexpression inhibitor.

Preferably, at least one cytostatic in conjunction with at least one overexpression inhibitor of DNA repair gene and/or oncogene or a drug containing the overexpression inhibitor was already used during chemotherapy.

As 5-substituted nucleoside, (E)-5-(2-bromovinyl)-2'-deoxyuridine (BVDU) is used, the protective forms, salts and/or prodrugs thereof being able to be used. An example of a prodrug of BVDU according to the invention is represented in the general formula I:

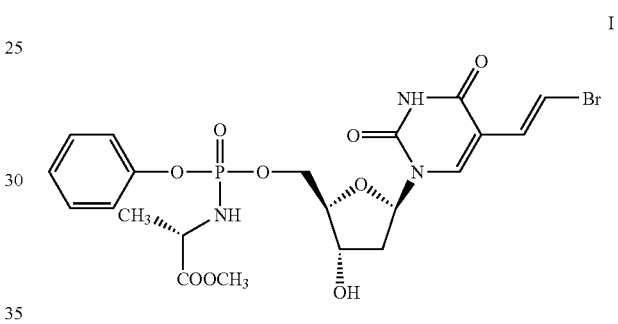

Preferably, the 5-substituted nucleoside is used in a dosage which leads to a blood concentration between 0.02 and 50 µg/ml.

Surprisingly, it was able to be shown that, after completion of chemotherapy, if the cells grow further solely with 5-substituted nucleoside (base analogues), the growth thereof is inhibited even more than if the chemotherapy had been continued with the cytostatics. Completely unexpectedly, the effect of the 5-substituted nucleosides (base analogues) increased instead of decreased.

This effect was established by means of a screening system according to the invention. This screening method is based on the treatment of tumour cells during a chemotherapy cycle over a period of preferably eight to thirty days with increasing doses of a cytostatic and a constant dose of the overexpression inhibitor. After this combination treatment, the cytostatic is discontinued and the treatment is continued solely with the overexpression inhibitor. This recovery phase (also called recovery phase) lasts preferably between 3 and 10 days. Chemotherapy cycles of this type can be implemented successively up to 6 times.

As a result, a constellation of treatment forms which was surprising for the person skilled in the art was produced.

5-substituted nucleosides, given alone, show no effect.
5-substituted nucleosides, given together with a cytostatic, show an effect.
5-substituted nucleosides, given alone, after they had been given in advance together with a cytostatic (recovery phase), show an increased effect.

The effect, i.e. the inhibition of chemoresistance and increase in chemosensitivity, can be described as a toxic maintenance of cytostatics-induced apoptosis by influencing the gene expression of specific genes. This takes place by
1. Blockade of "survival pathways" in the recovery phase.
2. Blockade of DNA repair of associated enzymes.
3. Induction of DT-diaphorase activity.
4. Reduced expression of ATP-generated enzymes in the recovery phase.

With respect to 1), base analogues such as BVDU block "survival pathways" principally in the recovery phase of the co-treatment after discontinuing the cytostatics and consequently enforce the course of apoptosis.

By means of HOPI double colouration of AH13r tumour cells of the rat, it was able to be detected that cytostatics such as doxorubicin (DOX), mitoxantrone (MXA) or mitomycin C (MMC) initiate apoptosis. Co-treatment with the base analogue (E)-5-(2-bromovinyl)-2'-deoxyuridine (BVDU) promotes apoptosis by blockade of anti-apoptotic "survival pathways" which include STAT3 and JUN-D.

This effect occurs firstly in the recovery phase of the cells, as can be seen in Example 2.

Constitutively activated STAT3 has an oncogenic effect and contributes to the development of different human cancer diseases. This occurs by inhibition of apoptosis. In this way, STAT3 facilitates the survival of tumour cells and makes cells resistant to a chemotherapy. Correspondingly, the inhibition of "STAT3 signalling" induces apoptosis and increases the sensitivity to cytostatics.

JUN-D, a member of the JUN gene family, is an essential component of the "activating protein-1" (AP-1) transcription factor complex with omnipresent expressivity. JUN-D$^{(-/-)}$ primary fibroblasts show premature ageing and increased apoptosis after UV radiation or TNFα treatment. This result leads to the supposition that JUN-D activates the "NFkappaB survival pathway". Furthermore, p202, which is regulated directly by JUN-D, makes fibroblasts able to resist apoptosis.

Co-treatment by BVDU reduced the expression of both JUN-D isoforms by approximately one quarter. In contrast, STAT3 was regulated in the recovery phase by approximately two thirds (Example 2).

The effect in the recovery phase after co-treatment with mytomycin C is particularly impressive. Here, the base analogue reduces the overexpression of the oncogene JUN-D to the control level (Example 2).

With respect to 2), base analogues such as BVDU block DDX1. DDX1 is co-amplified with MYCN and overexpressed in neuroblastoma (NB) and retinoblastoma cell lines and tumours. NB patients with amplification of both DDX1 and MYCN have a poorer prognosis than patients with only MYCN gene amplification. DDX1 has therefore oncogenic potential.

Co-treatment of MMC with BVDU reduces the overexpression of UBE2N and APEX by approximately one third. Modifications of UBE2N influence the resistance to DNA damage. APEX nuclease is a DNA repair enzyme. Blockade of the APEX expression doubles the cell lysis and increases DNA breakages.

With respect to 3), BVDU induces DT-diaphorase (Example 3). The latter has two properties which are important for the chemotherapy. It activates, on the one hand, cytostatics from the class of quinones and, on the other hand, reduces non-specific toxic effects which are based on the production of reactive oxygen species.

Absence of the DT-D gene leads by reduced p53 and p73 expression to myeloid hyperplasia and correspondingly to reduced apoptosis rates. This is in accord with the observation that a multifactorial "multidrug resistance" phenotype of tumour cells involves a reduction and no increase in DT-diaphorase expression. Interestingly, the DT-D enzyme activity also stabilises the lymphocyte populations. This effect could have an advantageous effect on the stabilisation of the immune system of patients during chemotherapy.

Many cytostatics, such as e.g. DOX and MXA, disrupt the redox status and the mitochondrial respiration of the cancer cell. This leads to the production of reactive oxygen species (ROS). Not only the cancer cell but also all other cells are affected by the sudden accumulation of ROS, as a result of which undesired side effects occur during chemotherapy.

DT-D inactivates ROS and thus protects cells from non-specific ROS and electrophilic attacks. As an index for this effect of BVDU on the reduction of undesired side effects during chemotherapy, the increase in weight of doxorubicin+BVDU-treated rats may be cited in Example 4. DOX treatment alone leads to weight losses because of the toxic side effects. It is certain that only the side effects (possibly the cardiotoxicity characteristic of DOX) are reduced by BVDU but not the toxic effects on the tumour.

With respect to 4), by altered expression of different enzymes in the recovery phase, the cytostatic effect is maintained also in the absence of a cytostatic. As can be seen in Example 5, the expression of eight genes is increased, that of six genes lowered.

The gene products influence the formation of microfilaments, differentiation, signal transduction and ATP generation.

The subject according to the invention is explained in more detail with reference to the following Figures and Examples without limiting said subject to the mentioned embodiments.

EXAMPLES

Example 1

BVDU treatment increases the sensitivity of AH13r sarcoma cells to chemotherapy-induced apoptosis. This effect is maintained even after discontinuation of the cytostatic in the so-called recovery phase.

Figure 1:
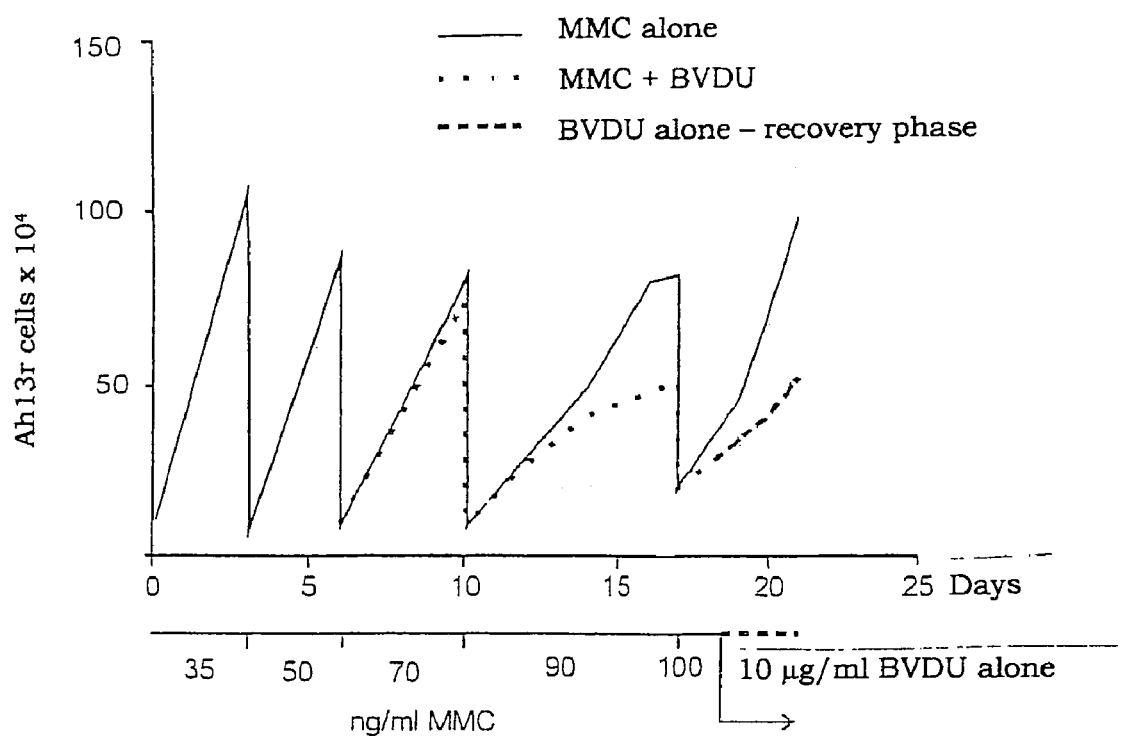
FIG. 1 shows the effect of a cytostatic alone and in combination with BVDU on the number of AH13r cells.

AH13r cells were subjected to increasing doses of the cytostatic mitomycin C (MMC). BVDU, given alone, showed no toxic effect. MMC+BVDU treatment led, after three treatment cycles, to reduction in the cell number in comparison to treatment with MMC alone. This inhibitory effect was maintained even after discontinuation of the cytostatic in the next cycle, in the so-called recovery phase. The cells without MMC and BVDU continued to grow without inhibition. However, those which continued to receive BVDU were greatly inhibited in their growth (see FIG. 1).

Figure 2:
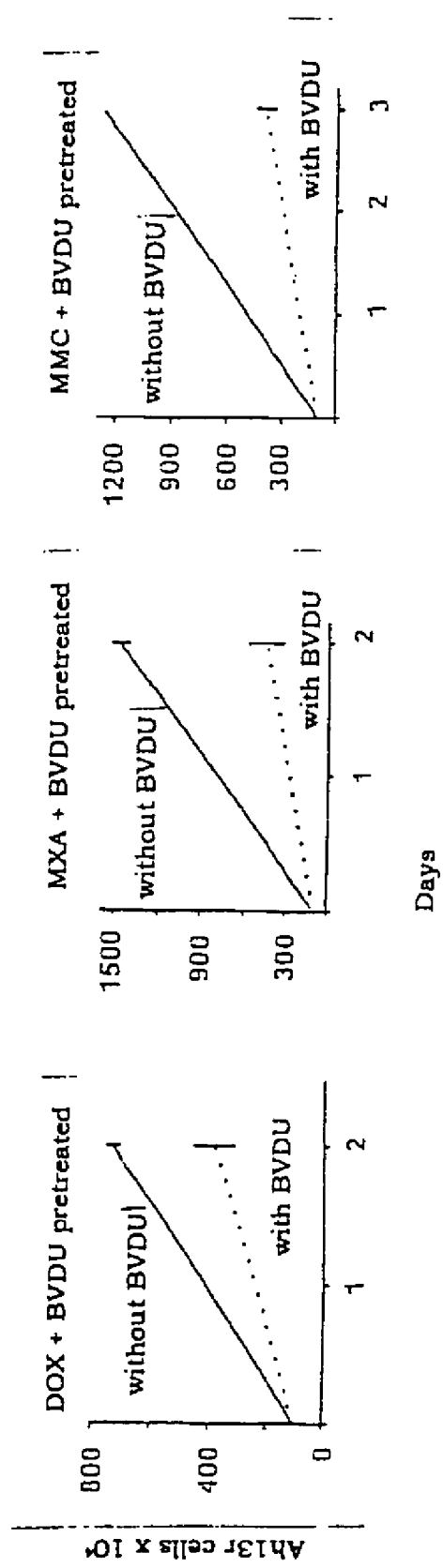
FIG. 2 shows, in comparison to FIG. 1, the results with doxorubicin (DOX), mitoxantrone (MXA) and methotrexate (MTX).

Corresponding results were achieved with methotrexate (MTX), doxorubicin (DOX) and mitoxantrone (MXA) (see FIG. 2).

The indication that the reduction in cell number is based on apoptosis, was detected by means of Hoechst 33258/propidium iodide (Hopi) double colouration.

Example 2

Figure 3:
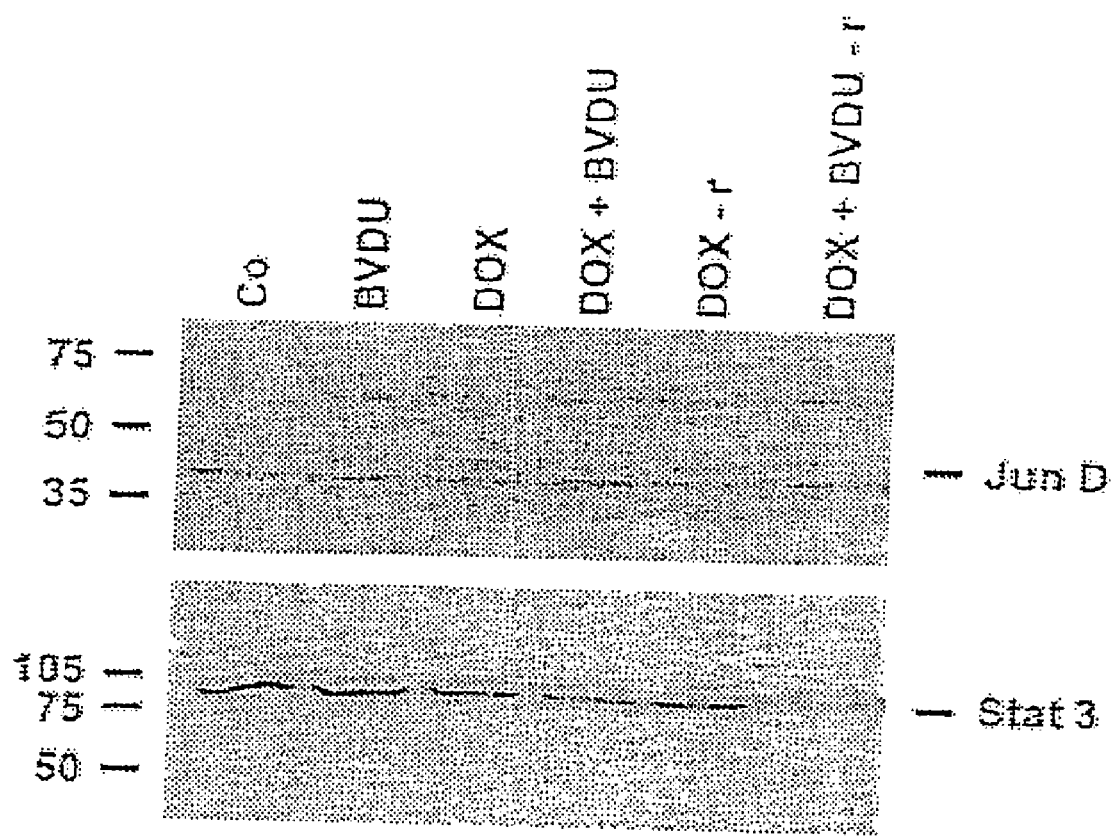
FIG. 3 shows a Western Blot analysis for testing the "survival pathways" with doxorubicin (DOX).

We tested different "survival pathways" by means of Western Blot analysis. The analyses were implemented according to standard methods, as is described in Sambrook et al., 2001, Molecular Cloning ($3^{rd}$ ed.). Antibody dilutions: P-STAT3 (cell signalling) 1:500, JUN-D (Santa Cruz, Calif.) 1:1,000. The upper of the two JUN-D bands shows the "full length isoform" and the lower band the "truncated isoform" which is 48 amino acids shorter. Both isoforms can activate the transcription, but the "full length" variant is more effective than the "truncated" isoform (cf. FIG. 3).

The densitometrically determined content of oncogene proteins JUN-D and STAT3 was reduced by a quarter or two thirds after DOX treatment in the recovery phase (r=recovery phase). In the "recovery" only BVDU is given, no cytostatic.

Figure 4:
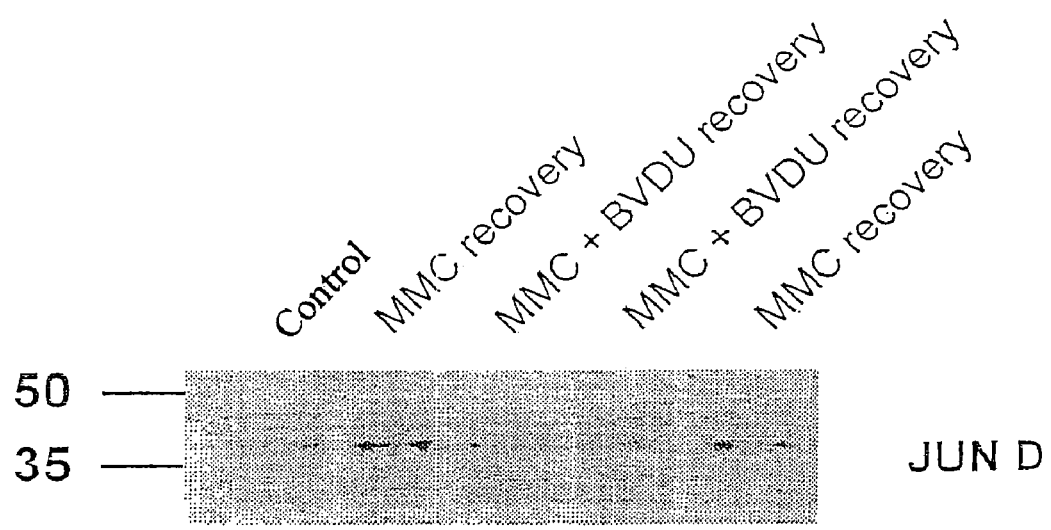
FIG. 4 shows tests with mitomycin (MMC) corresponding to FIG. 3.

A corresponding result was achieved in the tests with mytomycin C (MMC) (see FIG. 4).

In the test with mytomycin C (MMC), BVDU, given in the "recovery", effected a complete inhibition of the MMC induced JUN-D overexpression to the control level.

Example 3

Figure 5:
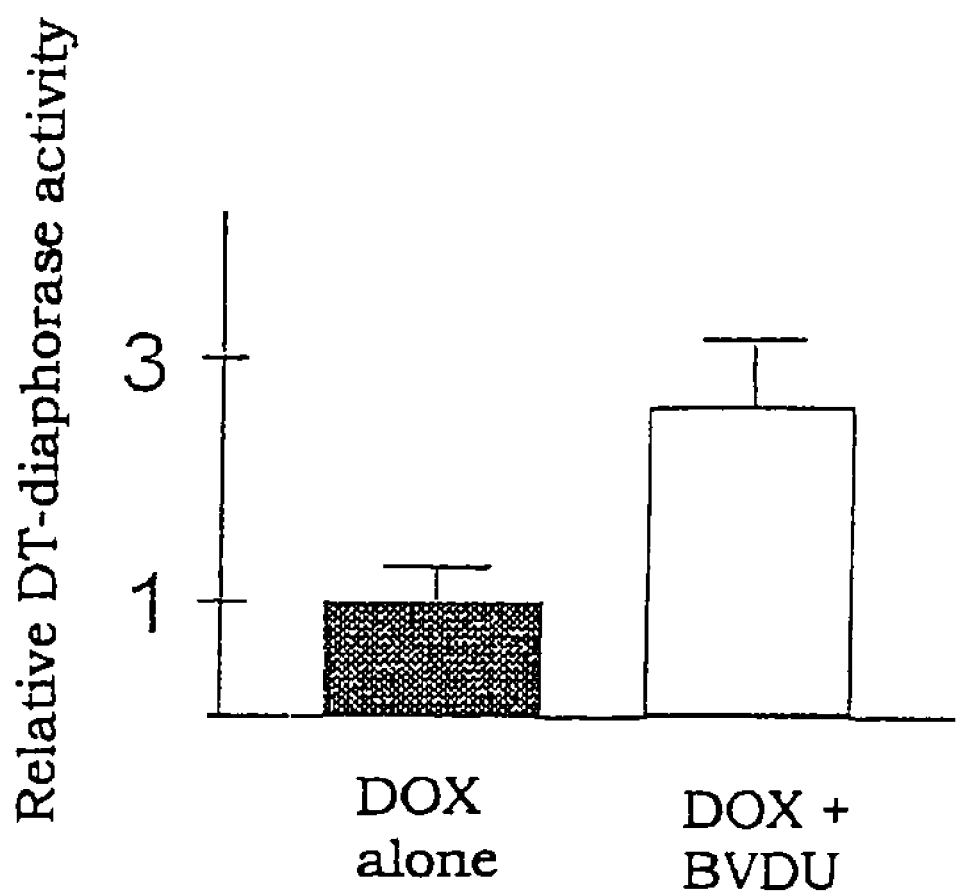
FIG. 5 shows the results of the measurement of DT-diaphorase (DT-D), doxorubicin (DOX) having been used alone or together with BVDU.

The measurement of the DT-diaphorase (DT-D) was effected as a dicoumarol-inhibitable NAD(P)H: dichlorophenol indophenol reductase, as described in Hodnick et al., Anal. Biochem 252(1), 1997, 165-168. We tested extracts of a similar number of cells which had been treated with DOX+/−BVDU for DT-D activity. Cells treated with BVDU showed an approximately threefold DT-D activity relative to the cells from the control group or from the group of cells treated solely with DOX (see FIG. 5).

Corresponding results were achieved with mitoxantrone (MXA) and methotrexate (MTX). BVDU alone increases the DT-D activity constantly, but in part only weakly.

Figure 6:
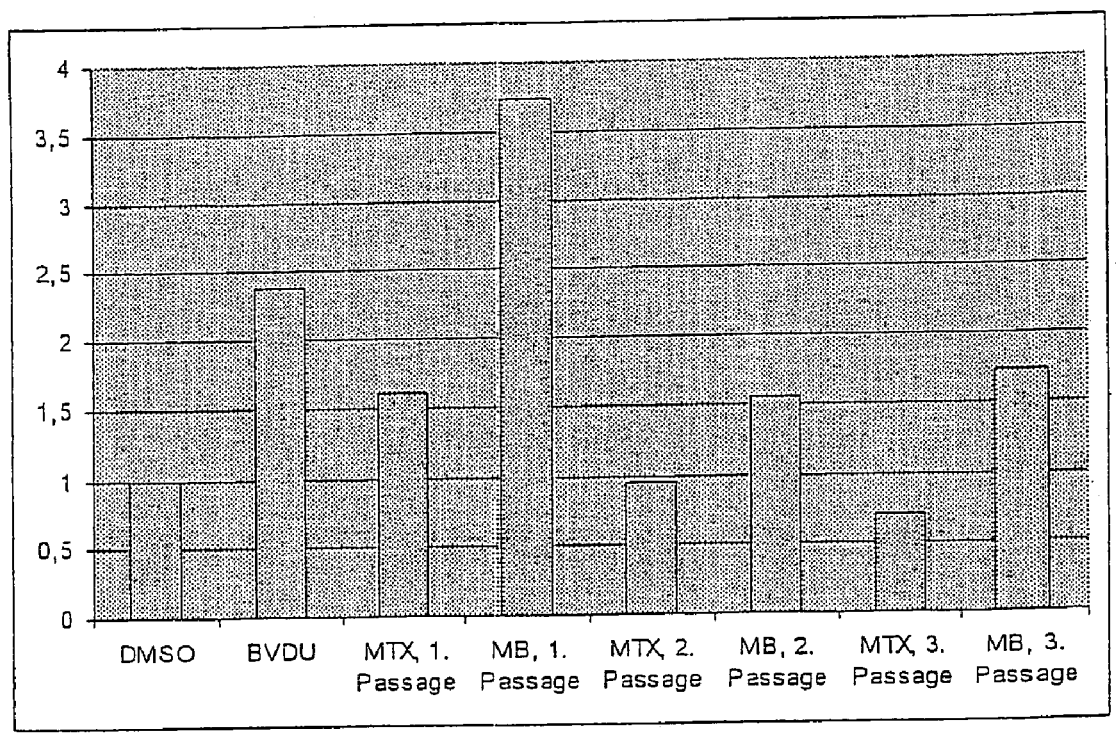
FIG. 6 shows tests with methotrexate (MTX) corresponding to FIG. 5.

The results with methotrexate (MTX) and human K562 tumour cells are cited in FIG. 6. MB means MTX and BVDU. Passage means dilution and conversion of the cells for further growth. The relative DT-D activity is illustrated on the Y axis.

Example 4

The reduction in toxic side effects of doxorubicin (DOX) was able to be shown in the test with rats (see Table 1). SD rats were treated with dimethybenzanthracene (DMBA). The consequently induced tumours were inhibited in their growth by DOX treatment (1 mg/kg). During the treatment and one day after each treatment, i.e. in the recovery phase, the animals obtained respectively 15 mg/kg BVDU.

TABLE 1

| Average of the data from 5-8 rats | Relative tumour size Day 1 | Relative animal weight Day 1 | Relative tumour size Day 16 | Relative animal weight Day 16 |
|---|---|---|---|---|
| Control | 1 | 0 | 6 | +7% |
| DOX alone | 1 | 0 | 1.5 | −7% |
| DOX + BVDU | 1 | 0 | 1 | +7% |

Example 5

Listing of the proteins influenced by the treatment with base analogues and mitomycin C. The results of the implementation of a two-dimensional gel electrophoresis are compiled in the following Table 2.

TABLE 2

| Protein | DMSO control | BVDU alone |
|---|---|---|
| DEAD/H BOX 1; DDX1 | 0.88 | 0.332 |
| | MMC alone | MMC + BVDU |
| MALATE-DEHYDROGENASE, SOLUBLE; MDH1 | 0.418 | 1.359 |
| MYOSIN, HEAVY CHAIN 1, NORMAL SIMILARITY, ADULT; MYH1 | 0.182 | 0.588 |
| UBIQUITIN-CONJUGATING ENZYME E2N; UBE2N | 0.669 | 0.178 |
| APURINIC ENDONUCLEASE; APE; APE1; APEX | 0.363 | 0.14 |
| | MMC "recovery", further cultivation without MMC and BVDU | MMC + BVDU "recovery", further treatment by BVDU alone |
| PLATELET-ACTIVATING FACTOR ACETYLHYDROLASE, ISOFORM 1B, ALPHA SUB-UNIT; PAFAH1B1 | 0.219 | 0.619 |
| U5 snRNP-SPECIFIC PROTEIN, 116-KD | 0.2 | 0.523 |
| HAEMOGLOBIN-BETA LOCUS; HBB | 0.088 | 0.502 |
| HAEMOGLOBIN-ALPHA LOCUS 1; HBA1 | 0.054 | 0.316 |
| ACTIN, BETA; ACTB | 0.163 | 0.451 |
| Similar to BETA-ACTIN | 0.096 | 0.357 |
| ACTIN similar | 0.112 | 0.398 |
| TROPOMODULIN 2; TMOD2 | 0.095 | 0.28 |

TABLE 2-continued

| Protein | | |
|---|---|---|
| SUCCINATE-DEHYDROGENASE COMPLEX, SUB-UNIT A, FLAVOPROTEIN; SDHA | 0.255 | absent |
| PYRUVATE-DEHYDROGENASE COMPLEX, E1-ALPHA POLYPEPTIDE 1; PDHA1 | 1.751 | 0.533 |
| TUBULIN, BETA-5 | 4.705 | 1.553 |
| POLY(rC)-BINDING PROTEIN 2; PCBP2 | 0.912 | 0.234 |
| MALATE-ENZYME 2; ME2 | 0.972 | 0.322 |
| Mini-chromosome preservation inadequate 7; MITOTIN, CELL CLASS CYCLE SIMILAR 1; CDCL1 | 0.374 | 0.119 |

The invention claimed is:

1. A method of increasing apoptotic effect of cytostatics after chemotherapy comprising administering (E)-5-(2-bromovinyl)-2'-deoxyuridine (BVDU), BVDU salt, or BVDU prodrug of the general formula I, or mixture thereof, the administering being without administration of a cytostatic, during a recovery phase after a cytostatic chemotherapy cycle, wherein the cytostatic chemotherapy cycle includes administration of (a) BVDU, prodrug of the general formula I, or BVDU salt, or mixture thereof and (b) a cytostatic

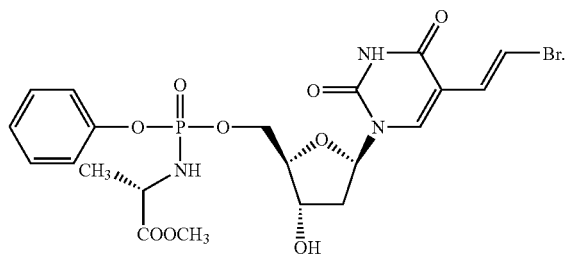

I

2. The method of claim 1 wherein during the cytostatic chemotherapy cycle, administered amounts of cytostatic are increased over a period of the cytostatic chemotherapy cycle, and the administered amount of BVDU, BVDU salt, or prodrug of general formula I, or mixture thereof is constant.

3. The method of claim 2 wherein the recovery phase has a duration of from 3 to 10 days.

4. The method of claim 2 wherein the cytostatic chemotherapy cycle has a duration of from 8 to 30 days.

5. The method of claim 1 comprising administering during the cytostatic chemotherapy cycle the BVDU prodrug of the general formula I:

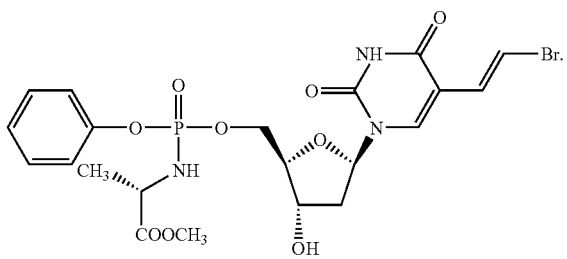

I

6. The method of claim 1 wherein the administration provides a 5-substituted nucleoside blood concentration between 0.02 and 50 µg/ml during the recovery phase.

7. The method of claim 1 wherein the cytostatic comprises doxorubicin, mitoxantrone, mitomycin C, or methotrexate.

8. The method of claim 7 wherein the administration provides a 5-substituted nucleoside blood concentration between 0.02 and 50 µg/ml during the recovery phase.

9. The method of claim 5 wherein the cytostatic comprises doxorubicin, mitoxantrone, mitomycin C, or methotrexate.

10. The method of claim 5 wherein the administration provides a 5-substituted nucleoside blood concentration between 0.02 and 50 µg/ml during the recovery phase.

11. The method of claim 5 wherein the administration provides a 5-substituted nucleoside blood concentration between 0.02 and 50 µg/ml during the cytostatic chemotherapy cycle.

12. The method of claim 5 wherein the recovery phase has a duration of from 3 to 10 days.

13. The method of claim 12 wherein the cytostatic chemotherapy cycle has a duration of from 8 to 30 days.

14. The method of claim 5 wherein the cytostatic chemotherapy cycle has a duration of from 8 to 30 days.

* * * * *